US011177028B2

(12) United States Patent
Suarez Saiz et al.

(10) Patent No.: US 11,177,028 B2
(45) Date of Patent: Nov. 16, 2021

(54) EXTRACTION, REPRESENTATION, AND COGNITIVE INTERPRETATION OF MEDICALLY RELEVANT EVIDENCE

(71) Applicant: International Business Machines Corporation, Armonk, NY (US)

(72) Inventors: Fernando Jose Suarez Saiz, Armonk, NY (US); Richard J Stevens, Monkton, VT (US); Corey Sanders, Hilliard, OH (US); Michael Britt, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 420 days.

(21) Appl. No.: 16/211,233

(22) Filed: Dec. 6, 2018

(65) Prior Publication Data

US 2020/0185072 A1    Jun. 11, 2020

(51) Int. Cl.
```
G16H 15/00    (2018.01)
G16H 50/20    (2018.01)
G16H 10/60    (2018.01)
G16H 10/20    (2018.01)
```
(52) U.S. Cl.
CPC ............ *G16H 15/00* (2018.01); *G16H 10/20* (2018.01); *G16H 10/60* (2018.01); *G16H 50/20* (2018.01)

(58) Field of Classification Search
None
See application file for complete search history.

(56) References Cited

U.S. PATENT DOCUMENTS

| 6,584,445 B2 | 6/2003 | Papageorge |
| 2004/0044547 A1 | 3/2004 | Klennert et al. |
| 2012/0016690 A1 | 1/2012 | Ramarajan et al. |
| 2012/0047105 A1* | 2/2012 | Saigal .................... G06F 19/00 706/52 |

(Continued)

FOREIGN PATENT DOCUMENTS

WO    2017007461 A1    1/2017

OTHER PUBLICATIONS

Morid et al., Classification of Clinically Useful Sentences in Clinical Evidence Resources, Jan. 13, 2016, Journal of Biomedical Informatics, 60 (2016) 14-22 (Year: 2016).*

(Continued)

*Primary Examiner* — Devin C Hein
(74) *Attorney, Agent, or Firm* — Patterson + Sheridan, LLP

(57) ABSTRACT

Techniques for cognitively interpreting comparative statements are provided. A corpus of documents associated with treatment of a first medical disorder is received. Relative efficacies for a plurality of therapies are determined by, for at least a first respective document in the corpus of documents, identifying and extracting, using one or more natural language processing techniques, a conclusion specified within natural language text of the respective document, where the conclusion includes a comparison between two or more therapies of the plurality of therapies, determining a sentiment of the extracted conclusion, with respect to at least one therapy of the plurality of therapies, and identifying one or more cohorts of patients that are associated with the conclusion. A knowledge graph is generated based on the relative efficacies.

20 Claims, 8 Drawing Sheets

(56) References Cited

U.S. PATENT DOCUMENTS

| | | | |
|---|---|---|---|
| 2013/0035956 A1* | 2/2013 | Carmeli | G06Q 10/10 705/3 |
| 2013/0041683 A1 | 2/2013 | Boissel | |
| 2016/0015493 A1 | 1/2016 | Ertl | |
| 2016/0154937 A1 | 6/2016 | Hennenfent | |
| 2016/0188813 A1 | 6/2016 | Hennenfent | |

OTHER PUBLICATIONS

Shi et al., Semantic Health Knowledge Graph: Semantic Integration of Heterogeneous Medical Knowledge and Services, Feb. 12, 2017, Hindawi BioMed Research International, vol. 2017, Article ID 2858423, 1-12, https://doi.org/10.1155/2017/2858423 (Year: 2017).*

Frizman et al., Interpreting Comparative Constructions in Biomedical Text, BioNLP 2007: Biological, translational, and clinical language processing, pp. 137-144, Prague, Jun. 2007 (Year: 2007).*

R Brian Haynes, Nancy L Wilczynski for the Hedges Team, "Optimal search strategies for retrieving scientifically strong studies of diagnosis from Medline: analytical survey," BMJ, doi: 10.1136/bmj.38068.557998.EE (published Apr. 8, 2004), 5 pages.

CureHunter | Real-Time Evidence Based Medicine [Accessed Online Nov. 26, 2018] http://www.curehunter.com/public/showTopPage.do.

Doctor Evidence—Transforming data into insights [Accessed Online Nov. 26, 2018] https://drevidence.com/.

F. Saiz, "First experiences with an AI-assisted clinical evidence system to evaluate clinical consensus among clinical trial publications." DOI: 10.1200/JCO.2018.36.15_suppl.e18583, Journal of Clinical Oncology, vol. 36, No. 15_suppl—published online before print, May 2018: 2018 ASCO Annual Meeting, e18583-e18583. <http://ascopubs.org/doi/abs/10.1200/JCO.2018.36.15_suppl.e18583>.

L. Chen, "MedRank: Discovering influential medical treatments from literature by information network analysis." In Proceedings of the Twenty-Fourth Australasian Database Conference—vol. 137 (ADC '13), Hua Wang and Rui Zhang (Eds.), vol. 137. Australian Computer Society, Inc., Darlinghurst, Australia, Australia, 3-12, 2013.

* cited by examiner

EXTRACTION, REPRESENTATION, AND COGNITIVE INTERPRETATION OF MEDICALLY RELEVANT EVIDENCE

BACKGROUND

The present disclosure relates to extracting and analyzing data, and more specifically, to extracting and cognitively interpreting medical evidence.

In a variety of domains, studies, experiments, and trials are performed to understand how potential options or selections interact and compare to each other. For example, in the medical field, studies and trials are performed to determine the efficacy of new and existing therapies, in order to determine the best practices for treating or curing illnesses or disorders. Frequently, the results of these studies, experiments, and trials are published for review by others. Currently, the published literature is reviewed manually by subject-matter experts (SMEs) to determine the state of the field, and provide guidance with respect to optimal therapies. However, these determinations are time-consuming, expensive, and inherently biased. Further, the published literature is expanding at an increasing and unprecedented rate. As the number of published documents increases, it has become impossible to aggregate and interpret them all. Thus, current guidelines and best practices are universally outdated, and potentially conflict with newly discovered therapies or interactions.

SUMMARY

According to one embodiment of the present disclosure, a method is provided. The method includes receiving a corpus of documents associated with treatment of a first medical disorder. The method further includes determining relative efficacies for a plurality of therapies by operation of one or more processors by, for at least a first respective document in the corpus of documents, (i) identifying and extracting, using one or more natural language processing techniques, a conclusion specified within natural language text of the respective document, wherein the conclusion includes a comparison between two or more therapies of the plurality of therapies, (ii) determining a sentiment of the extracted conclusion, with respect to at least one therapy of the plurality of therapies, and (iii) identifying one or more cohorts of patients that are associated with the conclusion. Finally, the method includes generating a knowledge graph based on the relative efficacies.

According to a second embodiment of the present disclosure, a computer program product is provided. The computer program product comprises a computer-readable storage medium having computer-readable program code embodied therewith. The computer-readable program code is executable by one or more computer processors to perform an operation comprising receiving a corpus of documents associated with treatment of a first medical disorder. The operation further includes determining relative efficacies for a plurality of therapies by operation of one or more processors by, for at least a first respective document in the corpus of documents, (i) identifying and extracting, using one or more natural language processing techniques, a conclusion specified within natural language text of the respective document, wherein the conclusion includes a comparison between two or more therapies of the plurality of therapies, (ii) determining a sentiment of the extracted conclusion, with respect to at least one therapy of the plurality of therapies, and (iii) identifying one or more cohorts of patients that are associated with the conclusion. Finally, the operation includes generating a knowledge graph based on the relative efficacies.

According to a third embodiment of the present disclosure, a system is provided. The system includes one or more computer processors, and a memory containing a program which when executed by the one or more computer processors performs an operation. The operation includes receiving a corpus of documents associated with treatment of a first medical disorder. The operation further includes determining relative efficacies for a plurality of therapies by operation of one or more processors by, for at least a first respective document in the corpus of documents, (i) identifying and extracting, using one or more natural language processing techniques, a conclusion specified within natural language text of the respective document, wherein the conclusion includes a comparison between two or more therapies of the plurality of therapies, (ii) determining a sentiment of the extracted conclusion, with respect to at least one therapy of the plurality of therapies, and (iii) identifying one or more cohorts of patients that are associated with the conclusion. Finally, the operation includes generating a knowledge graph based on the relative efficacies.

DETAILED DESCRIPTION

Figure 1:
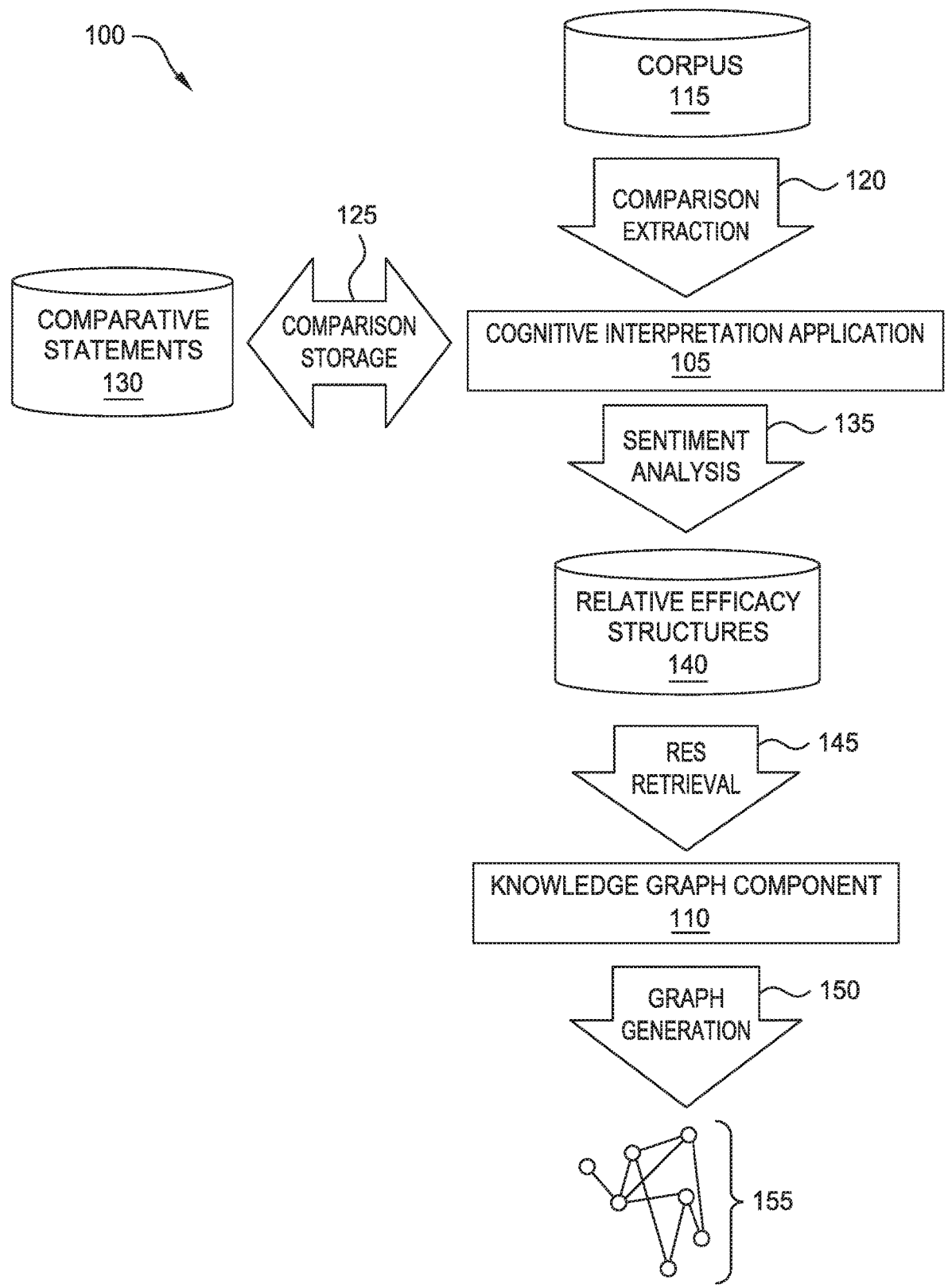
FIG. 1 illustrates a workflow for cognitively determining the relative efficacy of therapies, according to one embodiment disclosed herein.

In an embodiment of the present disclosure, techniques for cognitive analysis, representation, and interpretation of published literature are provided. In one embodiment, a corpus of medical literature is parsed and analyzed to identify and extract comparative statements or opinions made by the authors of the paper. For example, in a conclusion or summary, the authors may indicate that a particular therapy showed improved results, as compared to one or more other therapies (or as compared to the known or popular literature and practices). These conclusions are provided in natural language text, and are rarely structured in a way that allows for easy ingestion of the information.

Embodiments of the present disclosure are discussed with reference to medical literature. However, these examples are not limiting on the present disclosure, and one of skill in the art will recognize other domains and literature that the present embodiments can be applied to.

In one embodiment, these comparative statements are interpreted to determine a sentiment of the statement, and the relative efficacy of each therapy discussed. In some embodiments, a data structure, referred to herein as a relative efficacy structure or RES, is generated to capture the natural language comparative statement in a useful format. For example, in one embodiment, the RES has a number of dimensions, including the directionality of the comparison (e.g., which therapy is superior), the magnitude of the difference, the particular outcome the statement refers to (e.g., survival, progression-free survival, remission, etc.), qualifiers of the statement (e.g., limitations or specifications), and the like. In an embodiment, each RES is also associated with a weight, which is based on a variety of factors related to the underlying comparative statement and the nature of the article it is contained in.

In one embodiment, if a comparison is found in one direction (e.g., that treatment A is better than treatment B), a complementary RES is created in the opposite direction (e.g., indicating that treatment B is worse than treatment A). In this way, queries for information for a given treatment or therapy can identify all documents that involve the therapy, regardless of whether the document deemed the therapy to be superior or inferior.

In some embodiments, a knowledge graph can be generated based on the determined relationships extracted from one or more published document. For example, in one embodiment, each node in the knowledge graph corresponds to a particular therapy, and each edge corresponds to one or more RESs. In this way, the knowledge graph can be interrogated or searched to identify optimal treatment options for a given patient, based on a tremendous variety of medical literature. In such an embodiment, patient outcomes are improved, as the current state of the literature can be captured and ingested into the knowledge graph rapidly, reducing or eliminating the need for SME review. Further, in embodiments, the RESs provide additional insight and knowledge that is not accessible or present in existing solutions. Thus, embodiments of the present disclosure enable high-precision searching, and allow users to analyze the literature at a more granular level.

In some embodiments, users can search or query the knowledge graph based on therapies, cohorts, disorders, and the like, to return a subset of the graph that is relevant to the search. Further, in some embodiments, nodes and/or connections can be selected to retrieve a link to any documents or published literature that was analyzed to create the node or edge. In this way, users can readily access the relevant literature, if they wish to investigate further or obtain more information about why the topology of the graph is shaped as it is, as well as why particular connections exist.

Embodiments of the present disclosure can be applied to extract and interpret comparative statements made in any field. In one embodiment, medical literature (e.g., published studies, trials, experiments, and the like) is ingested. In some embodiments, the literature is analyzed to identify comparisons or statements about relative efficacy between therapy options. In an embodiment, a therapy is any treatment used to treat a disorder. As used herein, therapies can include drugs, medications, exercises, surgeries, use of equipment, prescribed activities, and the like. Further, in embodiments, therapies can include refraining from certain activities and withdrawing or reducing treatments. Additionally, in embodiments, a therapy may include multiple treatments or prescribed activities (e.g., multiple medications). As used herein, a medical disorder can include any illness or medical condition, including but not limited to mental or physical disease, sickness, disability, infection, symptoms, conditions, or statuses.

FIG. 1 illustrates a workflow 100 for cognitively determining the relative efficacy of therapies, according to one embodiment disclosed herein. In the illustrated embodiment, a Cognitive Interpretation Application 105 analyzes documents to extract Comparative Statements 130 and generate RESs 140, and a Knowledge Graph Component 110 analyzes these RESs 140 to generate a Knowledge Graph 150. In some embodiments, a Knowledge Graph 150 is generated to aid visualization or understanding of the literature (although it may not actually be displayed). In some embodiments, however, the knowledge graph is not created, and the RESs 140 are used for other purposes. That is, in some embodiments, the generated RESs are usable or searchable by other systems or components, and can be utilized to aid understanding and improve treatment selection, without the construction of a knowledge graph.

In the illustrated workflow 100, the Cognitive Interpretation Application 105 analyzes a Corpus 115 of documents to perform Comparison Extraction 120. In an embodiment, the Corpus 115 includes documents which include at least some portion of natural language text, which may or may not have comparative statements by the author(s). In some embodiments, the Corpus 115 corresponds to a particular domain of interest to a user. For example, in one embodiment, a larger corpus or collection of documents is searched to identify a subset of the documents that relate to a particular disorder, therapy, or set of disorders or therapies. In such an embodiment, this subset of documents makes up the Corpus 115. In some embodiments, the workflow 100 is performed on multiple corpora (e.g., once for each therapy or disorder).

In an embodiment, the Comparison Extraction 120 comprises utilizing one or more natural language processing (NLP) techniques to identify comparative statements in the text included in the Corpus 115. For example, in one embodiment, the Cognitive Interpretation Application 105 searches for comparative language (such as "superior," "better," "worse," "improved," and the like). In some embodiments, the Cognitive Interpretation Application 105 analyzes predefined sections of the documents to identify these comparative statements (e.g., the abstract, conclusion, methods, discussion, etc.). That is, in an embodiment, a user or administrator can specify portions or sections in the documents that should be analyzed. In other embodiments, the Cognitive Interpretation Application 105 analyzes the full text of the document. In one embodiment, the Cognitive Interpretation Application 105 first searches the identified sections (as identified by their headings or by metadata tags), and only parses the rest of the document if the specified section(s) do not include any comparative statements (or if the specified section(s) cannot be found or do not exist in the document).

In some embodiments, the Comparison Extraction 120 also includes remedying unknown terms in the statement, such as through disambiguation and acronym resolution. For example, if the comparative statement includes an acronym, in one embodiment, the Cognitive Interpretation Application 105 can expand the acronym. Similarly, if the statement includes ambiguous or general language (such as, "all treatments studied herein", "with respect to the relevant cohort," or "generic chemotherapy drugs"), the Cognitive Interpretation Application 105 can determine a meaning for the terms. In some embodiments, the Cognitive Interpretation Application 105 first parses the selected document to identify the meaning of the term. That is, the Cognitive Interpretation Application 105 attempts to find meaning for the unknown term by analyzing the text of the document in which the comparative statement was found using NLP techniques. If no satisfactory disambiguation is found (e.g., the confidence level of any potential disambiguations is below a threshold), the Cognitive Interpretation Application 105 can access other literature (or one or more knowledge graphs) to disambiguate the term. In some embodiments, if the true meaning is not found within the corresponding document, the confidence or weight of the extracted comparison is reduced.

In some embodiments, Comparison Extraction 120 includes annotation of the extracted comparative statements. For example, in one embodiment, the Cognitive Interpretation Application 105 utilizes one or more NLP techniques to identify the therapy or therapies involved in the statement, the qualifier or comparative term utilized, and the like. In some embodiments, the Cognitive Interpretation Application 105 also determines the cohort(s) to which the statement(s) apply, as discussed in more detail below. Additionally, in some embodiments, the Cognitive Interpretation Application 105 determines characteristics of the comparative statements, such as where in the text it was located (e.g., which section it was found in), the publication date of the document, whether the document has been peer-reviewed, an identity of the publisher or entity that provided the document, and the like.

In the illustrated embodiment, the Cognitive Interpretation Application 105 stores the extracted comparisons (e.g., the natural language text) in a data store for Comparative Statements 130. In some embodiments, these stored Comparative Statements 130 are annotated to identify the relevant therapies, qualifiers, and the like. In some embodiments, the Comparative Statements 130 also indicate the disorder that is relevant to the comparison. In other embodiments, the disorder is described by the cohort and/or cohort qualifiers. In embodiments, the Comparative Statements 130 can be stored locally by the Cognitive Interpretation Application 105, or in one or more remote storage locations (such as in the cloud). As illustrated, the Cognitive Interpretation Application 105 then performs Sentiment Analysis 135 on the extracted Comparative Statements 130, to generate a set of RESs 140. In an embodiment, this Sentiment Analysis 135 includes classifying each statement as positive, negative, or neutral with respect to each of the implicated therapies. In some embodiments, the Cognitive Interpretation Application 105 also determines a degree of the sentiment (based on, for example, the strength of the language or term used). Further, in some embodiments, the RESs 140 include an indication as to which outcome or outcome type the comparison relates to (e.g., overall survival, progression-free survival, etc.).

In some embodiments, the RESs 140 include an indication as to the therapies involved, the relevant cohort, and the like. In one embodiment, each RES 140 corresponds to a particular Comparative Statement 130. In one embodiment, each RES 140 is weighted based on a variety of factors. For example, in an embodiment, the weighting factors include how recently the corresponding document was published, whether the document has been peer-reviewed, the identity of the publisher or provider for the document, the number of patients evaluated in the clinical study, and the like. In one embodiment, publishers are associated with predefined weights or strengths, based on their prestige or trustworthiness. In some embodiments, the Cognitive Interpretation Application 105 weights each RES 140 based on a confidence level as well. In one embodiment, this confidence level is based in part on a confidence value returned by the NLP models. Further, in an embodiment, the confidence is adjusted based on where in the document the corresponding Comparative Statement 130 was found. For example, a comparison found in the abstract or conclusion can be given a higher weight, while a comparison found elsewhere in the document can be given a lower weight.

In the illustrated embodiment, the Knowledge Graph Component 110 retrieves these RESs 140 from the data store, and performs Graph Generation 150 to generate a Knowledge Graph 155. In an embodiment, each node in the Knowledge Graph 150 is a therapy (or combination of therapies), and each edge is based on the determined relationships and relative efficacies (e.g., the RESs 140). In one embodiment, the Knowledge Graph Component 110 adds an edge or connection for each determined RESs 140 (e.g., for each comparative statement found). In some embodiments, the Knowledge Graph Component 110 aggregates the comparisons. For example, in an embodiment, for each outcome type and cohort combination, the Knowledge Graph Component 110 can aggregate the corresponding RESs 140, in order to determine an overall relative efficacy for the therapies, with respect to the cohort and outcome. In some embodiments, this aggregation is based in part on the weights of each comparison, as discussed above.

Figure 2:
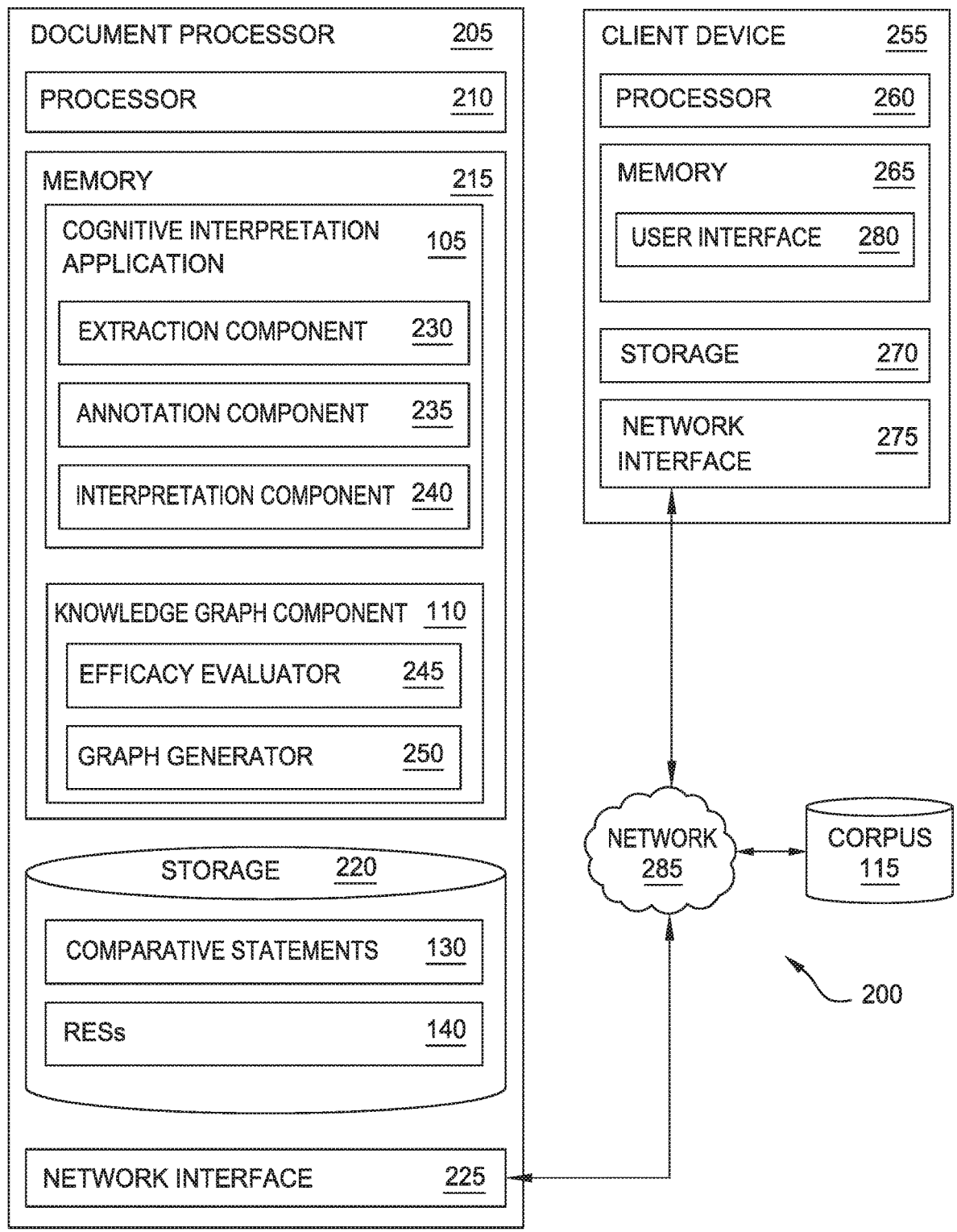
FIG. 2 is a block diagram of a system configured to cognitively determine the relative efficacy of therapies, according to one embodiment disclosed herein.

FIG. 2 is a block diagram of a system 200 configured to cognitively determine the relative efficacy of therapies, according to one embodiment disclosed herein. In the illustrated embodiment, the system 200 includes a Document Processor 205, a Client Device 255, and a Corpus 115. Although illustrated as discrete components, in embodiments, the Document Processor 205, Client Device 255, and Corpus 115 may operate or reside on a single device, or may be distributed across any number of devices. As illustrated, the Document Processor 205, Client Device 255, and Corpus 115 are communicatively linked through a Network 285. In one embodiment, the Network 285 is the Internet. Additionally, though a single Corpus 115 is illustrated, in embodiments, any number of corpora may be analyzed by the Document Processor 205.

As illustrated, the Document Processor 205 includes a Processor 210, a Memory 215, and Storage 220. In the illustrated embodiment, Processor 210 retrieves and executes programming instructions stored in Memory 215 as well as stores and retrieves application data residing in Storage 220. Processor 210 is representative of a single CPU, multiple CPUs, a single CPU having multiple processing cores, and the like. Memory 215 is generally included to be representative of a random access memory. Storage 220 may be a disk drive or flash-based storage device, and may include fixed and/or removable storage devices, such as fixed disk drives, removable memory cards, or optical storage, network attached storage (NAS), or storage area-network (SAN). Via the Network Interface 225, the Document Processor 205 can be communicatively coupled with corpuses of documents (such as Corpus 115), Client Devices 255, and the like.

In the illustrated embodiment, the Storage 220 of the Document Processor 205 includes a set of Comparative Statements 130 and RESs 140. In some embodiments, as discussed above, the Comparative Statements 130 and/or RESs 140 may be stored in one or more remote storage locations, such as in the cloud. As discussed above, in an embodiment, the Comparative Statements 130 are annotated natural language text extracts from documents in the Corpus 115. In one embodiment, each Comparative Statement 130 includes a comparison or opinion of the author of the corresponding document. In some embodiments, the annotations indicate the qualifier or comparator used by the author, the therapies implicated by the statement, the cohort or cohort qualifiers that limit the applicability of the comparison, and the like. Further, in some embodiments, the Comparative Statements 130 include publication characteristics of the statements, such as the location in their corresponding documents where they were found, the date of the publication, the entity that published it, and the like. Additionally, in one embodiment, the Comparative Statements 130 include an indication as to the confidence value that the NLP model(s) generated when parsing the statements.

As discussed above, in one embodiment, each RES 140 is a data structure representing a particular Comparative Statement 130. In some embodiments, each RES 140 indicates the therapies involved, the directionality or sentiment of the comparison, the cohort implicated, and the like. Further, in an embodiment, each RES 140 includes a weight, which can be based on a variety of factors including the publication characteristics of the underlying Comparative Statement 130, the confidence of the NLP model(s), and the like. In some embodiments, the RESs 140 are configured to be searchable, such that other systems or components (such as the Knowledge Graph Component 110) can readily access the information, and obtain an up-to-date and comprehensive understanding of the current state of the literature.

In the illustrated embodiment, the Memory 215 of the Document Processor 205 includes a Cognitive Interpretation Application 105 and a Knowledge Graph Component 110. The Cognitive Interpretation Application 105 includes an Extraction Component 230, an Annotation Component 235, and an Interpretation Component 240. Although depicted as discrete components for illustration, in embodiments, the operations and functionality of the Extraction Component 230, Annotation Component 235, and Interpretation Component 240 can be combined or divided across any number of components. Further, although depicted as software components residing in Memory 215, in embodiments, the operations and functionality of the Extraction Component 230, Annotation Component 235, and Interpretation Component 240 can be implemented using hardware, software, or a combination of hardware and software.

In an embodiment, the Extraction Component 230 identifies and extracts statements that include comparisons between therapies or treatment options from documents in the Corpus 115, as discussed above. In some embodiments, the Extraction Component 230 utilizes one or more NLP techniques or models to identify the relevant text. Further, in an embodiment, the Annotation Component 235 annotates the extracted statements. In one embodiment, the Annotation Component 235 utilizes predefined rules, and/or additional NLP models and/or techniques to annotate the statements. These annotated statements are then stored in the Comparative Statements 130. In this way, the textual comparisons found in the Corpus 115 are organized and represented in the Storage 220.

In the illustrated embodiment, the Interpretation Component 240 retrieves these Comparative Statements 130 and performs logical interpretation or sentiment analysis on them. In one embodiment, the Interpretation Component 240 classifies each Comparative Statement 130 as positive, negative, or neutral, with respect to each pair of involved therapies or treatments. For example, if the statement is that "treatment A led to better results than treatment B," the Interpretation Component 240 can determine that the comparison is positive with respect to treatment A, and negative with respect to treatment B. Similarly, if the statement is "treatments C and D were both inferior to treatment E," the Interpretation Component 240 determines that, as between therapies C and D, the sentiment is "neutral" or equal. However, as between treatment E and treatments C and D, the sentiment is positive. In this way, the Interpretation Component 240 determines the efficacy of each therapy, as compared to one or more other therapies in the statement.

In one embodiment, the Interpretation Component 240 also generates RESs 140 based on this analysis, as discussed below in more detail. That is, in an embodiment, the Interpretation Component 240 generates an organized and defined data structure that includes the relevant information from the textual Comparative Statement 130. In some embodiments, the Interpretation Component 240 generates a single RES 140 for each Comparative Statement 130. For example, in such an embodiment, if the sentiment is that treatment A is better than treatment B, the Interpretation Component 240 will generate a RES 140 indicating that treatment A is positive with respect to treatment B. In some embodiments, the Interpretation Component 240 also generates a second RES 140 indicating that treatment B is negative with respect to treatment A.

In the illustrated embodiment, the Knowledge Graph Component 110 generally retrieves the RESs 140 from Storage 220, and generates one or more knowledge graphs. As illustrated, the Knowledge Graph Component 110 includes an Efficacy Evaluator 245, and a Graph Generator 250. Although depicted as discrete components for illustration, in embodiments, the operations and functionality of the Efficacy Evaluator 245 and Graph Generator 250 can be combined or divided across any number of components. Further, although depicted as software components residing in Memory 215, in embodiments, the operations and functionality of the Efficacy Evaluator 245 and Graph Generator 250 can be implemented using hardware, software, or a combination of hardware and software. In an embodiment, the Efficacy Evaluator 245 retrieves and evaluates the RESs 140. For example, in one embodiment, the Efficacy Evaluator 245 searches for RESs 140 relating to one or more disorders or therapies that a user or administrator has selected. In other embodiments, the Efficacy Evaluator 245 retrieves and evaluates all available RESs 140. In an embodiment, the evaluation includes determining whether each RES 140 is already included in the knowledge graph.

Additionally, in some embodiments, the Efficacy Evaluator 245 aggregates the RESs 140 as appropriate, to determine an overall relative efficacy for each set of therapies. For example, in one embodiment, the Efficacy Evaluator 245 identifies RESs 140 with the same endpoints (e.g., that involve the same set of therapies) and aggregates them based on their respective weights to generate an overall relative efficacy between the therapies. In an embodiment, the Graph Generator 250 generates, inserts, and updates or refines nodes and edges in the knowledge graph, based on the evaluation provided by the Efficacy Evaluator 245. In some embodiments, the Graph Generator 250 and/or Efficacy Evaluator 245 aggregate the data by identifying all RESs 140 involving the same pair of therapies and including them in the graph, in order to capture all available evidence that compares the therapies without attempting to establish whether one is overall superior to the other.

In the illustrated embodiment, the Client Device 255 includes a Processor 260, a Memory 265, and Storage 270.

In the illustrated embodiment, Processor 260 retrieves and executes programming instructions stored in Memory 265 as well as stores and retrieves application data residing in Storage 270. Processor 260 is representative of a single CPU, multiple CPUs, a single CPU having multiple processing cores, and the like. Memory 265 is generally included to be representative of a random access memory. Storage 270 may be a disk drive or flash-based storage device, and may include fixed and/or removable storage devices, such as fixed disk drives, removable memory cards, or optical storage, network attached storage (NAS), or storage area-network (SAN). Via the Network Interface 275, the Client Device 255 can be communicatively coupled with corpuses of documents (such as Corpus 115), Document Processor 205, and the like.

As illustrated, the Memory 265 of the Client Device 255 includes a User Interface 280 for interacting with the Corpus 115 and/or Document Processor 205. In an embodiment, the User Interface 280 includes a graphical user interface (GUI) that lets users or administrators retrieve and review documents in the Corpus 115. In some embodiments, the User Interface 280 also allows the user to select a subset of the Corpus 115 (e.g., via search queries) to be processed by the Document Processor 205.

Although not illustrated, in embodiments, the Cognitive Interpretation Application 105 and Knowledge Graph Component 110 each provide one or more application programming interfaces (APIs) that allow the user (through the User Interface 280) to control the operations of the components. For example, in an embodiment, the user can use the User Interface 280 and APIs to indicate the set of documents to be analyzed, and to adjust any settings or configurations of the Cognitive Interpretation Application 105. Further, in an embodiment, the User Interface 280 and APIs enable the user to review the Comparative Statements 130 and/or RESs 140. Additionally, in an embodiment, the User Interface 280 and APIs allow the user to direct the Knowledge Graph Component 110 to generate one or more knowledge graphs based on the RESs 140, and to analyze and parse the generated graphs.

Figure 3A:
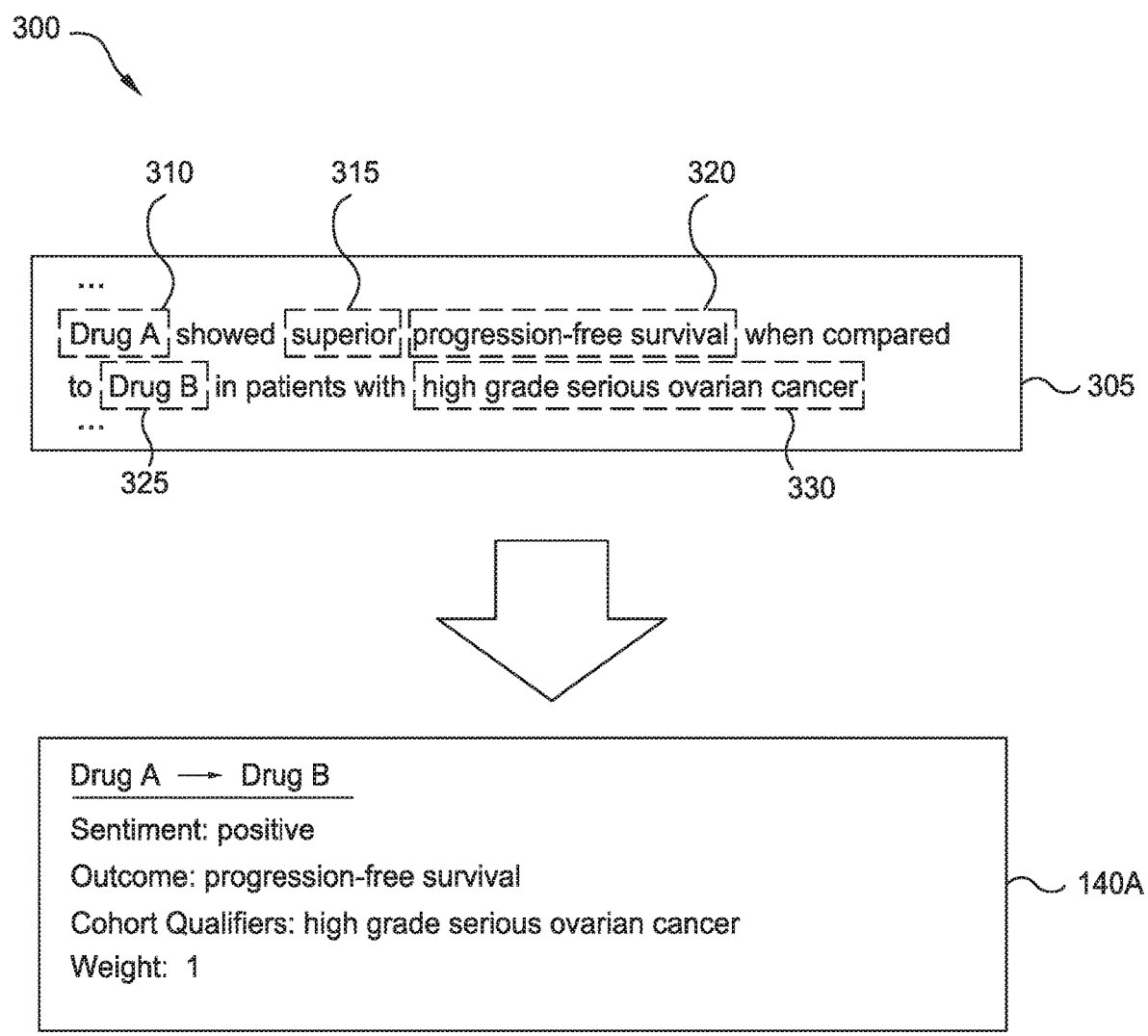
FIG. 3A is a workflow for determining the efficacy for a therapy, as compared to a different therapy, according to one embodiment disclosed herein.

FIG. 3A illustrates a workflow 300 for determining the efficacy for a therapy, as compared to a different therapy, according to one embodiment disclosed herein. In the illustrated workflow 300, a comparative statement (included in an Excerpt 305) is annotated with Annotations 310, 315, 320, 325, and 330. As illustrated by the ellipses above and below the comparative statement, the original document can be any size or length. In an embodiment, the Excerpt 305 was extracted from a document (e.g., by the Extraction Component 230) based on determining that it included a comparative statement.

In the illustrated embodiment, the Excerpt 305 was annotated by the Annotation Component 235, using one or more NLP techniques. As illustrated, Annotations 310 and 325 indicate the therapies mentioned or implicated by the statement. In one embodiment, these therapies are identified based on identifying the subject and object of the statement. Further, as illustrated, the Annotation 320 indicates the outcome (also referred to as the type) that is relevant to the statement. That is, in the illustrated embodiment, the Excerpt 305 discusses the relative efficacy of Drug A and Drug B, with respect to progression-free survival. Additionally, the Annotation 315 indicates the comparator (also referred to as qualifier or type qualifier), which indicates the comparison or statement being made (e.g., that the outcome, progression-free survival, was "superior."). Finally, as illustrated, the Annotation 330 corresponds to the cohort (or cohort qualifier) that the statement applies to.

In the illustrated embodiment, each of the relevant factors (e.g., Annotations 310, 315, 320, 325, and 330) are included within the same Excerpt 305. In embodiments, however, one or more of the relevant pieces of information can be located outside of the Excerpt 305. For example, in an embodiment, the cohort may be specified elsewhere in the document, and not explicitly given in the Excerpt 305. Similarly, one or more of the therapies or outcomes can be given elsewhere. For example, suppose the statement included "therapy Y led to the best results for the patients included in this study." In such an embodiment, the Extraction Component 230 and/or Annotation Component 235 can look elsewhere to determine the other therapy, the cohort, and the particular outcome type. Further, in an embodiment, the excerpt may only summarize one of the therapies in question and the Annotation Component 235 may look elsewhere to determine the complete definition of the therapy. For example, an excerpt may refer to "drug X-based therapy," where all of the components of this therapy are defined elsewhere in the document.

For example, the other therapies being tested may be listed in an introductory section, the cohort can be determined based on analyzing the patients involved, and the outcome of interest can be identified based on other sections of the document. In some embodiments, if the relevant information is not contained within the Excerpt 305, the confidence or weight of the comparative statement is reduced. In some embodiments, the Extraction Component 230 and/or Annotation Component 235 identify both the cohort (e.g., the patient population being studied) as well as cohort qualifiers (e.g., additional restrictions or limitations defining the group to whom the comparison is relevant). In one embodiments, the relevant cohort can identified based on other portions of the document (e.g., based on the abstract or study definitions). For example, a section of the document can indicate that the patients studied included females, aged 65-80, with hypertension. Additionally, the cohort qualifier ("high grade serious ovarian cancer") further restricts or limits the cohort to which the comparison is applicable.

As illustrated, the Cognitive Interpretation Component 105 (e.g., the Sentiment Component 240) then generates a RES 140A, based on the comparative statement. In the illustrated embodiment, as indicated by the arrow from Drug A to Drug B, the RES 140A indicates the relative efficacy of Drug A, as compared to Drug B. As illustrated, the sentiment is "positive," indicating that Drug A is better than Drug B with respect to the indicated cohort and the indicated outcome. Further, as illustrated, the outcome is "progression-free survival," and the cohort is individuals with "high grade serious ovarian cancer." As discussed above, in embodiments, this cohort can include additional attributes or definition, in combination with the cohort qualifiers found in the statement. Additionally, in the illustrated embodiment, the RES 140A includes a weight. In embodiments, this weight is based on a variety of factors, including the confidence of the NLP, the publication characteristics of the document, and the like.

Figure 3B:
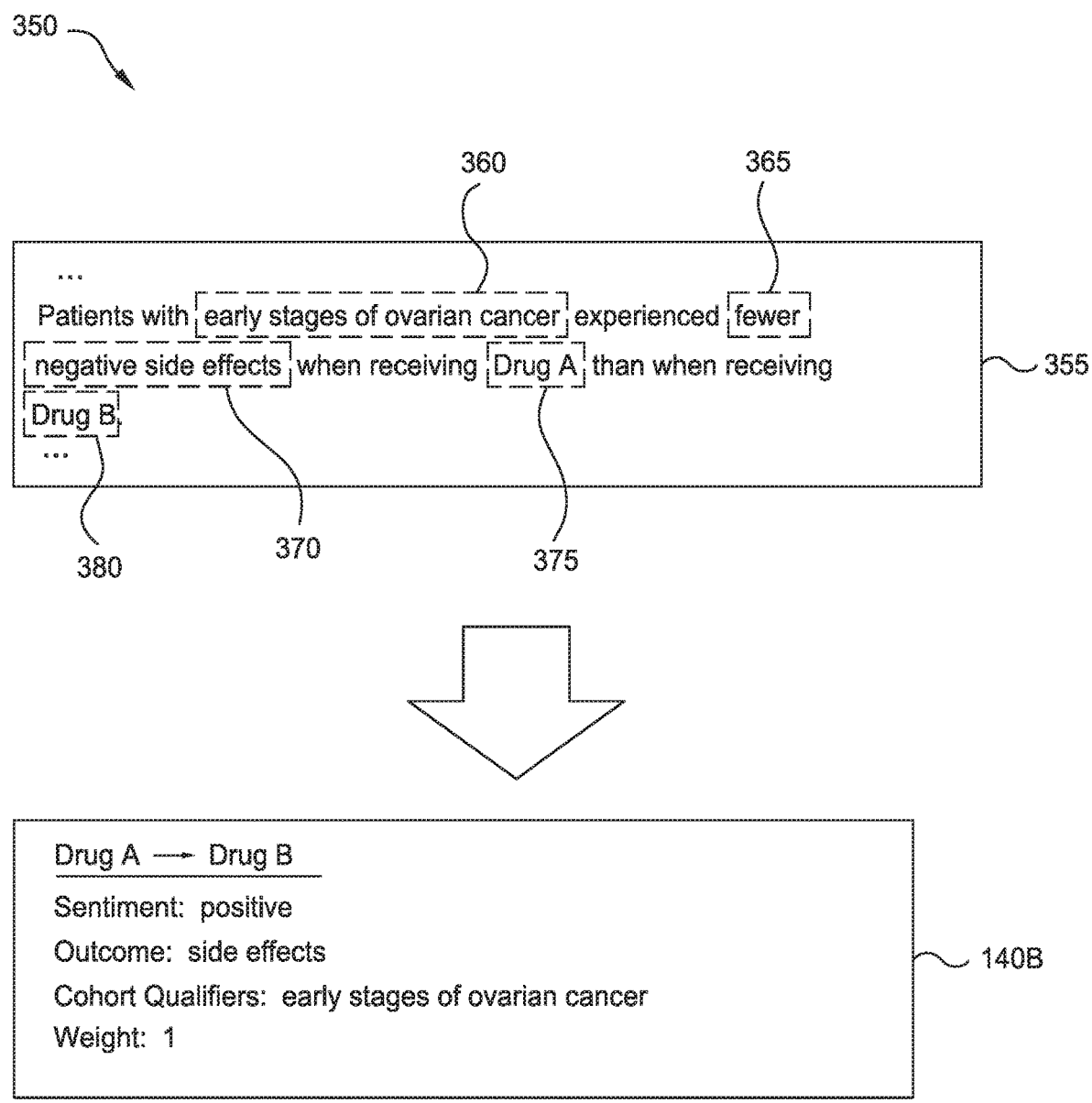
FIG. 3B illustrates a workflow for determining the efficacy for a therapy, as compared to a different therapy, according to one embodiment disclosed herein.

FIG. 3B illustrates a workflow 350 for determining the efficacy for a therapy, as compared to a different therapy, according to one embodiment disclosed herein. In the illustrated workflow 350, a comparative statement (included in an Excerpt 355) is annotated with Annotations 360, 365, 370, 375, and 380. As illustrated by the ellipses above and below the comparative statement, the original document can be any size or length. In an embodiment, the Excerpt 355 was extracted from a document (e.g., by the Extraction Component 230) based on determining that it included a comparative statement.

In an embodiment, the Excerpt 355 was annotated by the Annotation Component 235, using one or more NLP techniques. In the illustrated embodiment, Annotations 375 and 380 indicate the therapies mentioned or implicated by the statement. In one embodiment, these therapies are identified using the NLP models or techniques. Further, as illustrated, the Annotation 370 indicates the outcome of interest (also referred to as the type) that is relevant to the statement. That is, in the illustrated embodiment, the Excerpt 355 discusses the relative efficacy of Drug A and Drug B, with respect to negative side effects. Additionally, the Annotation 365 indicates the comparator (also referred to as qualifier or type qualifier), which indicates the comparison or statement being made (e.g., that the outcome, negative side effects, was "fewer."). Finally, as illustrated, the Annotation 360 corresponds to the cohort (or cohort qualifier) that the statement applies to.

As illustrated, the Cognitive Interpretation Component 105 (e.g., the Sentiment Component 240) then generates a RES 140B, based on the comparative statement. In the illustrated embodiment, as indicated by the arrow from Drug A to Drug B, the RES 140B indicates the relative efficacy of Drug A, as compared to Drug B. As illustrated, the sentiment is "positive," indicating that Drug A is better than Drug B with respect to the indicated cohort and the indicated outcome. That is, because the outcome itself is negative, the Sentiment Component 240 determines that a "worse" result in terms of the number or magnitude of side effects is, in fact, a positive result. Further, as illustrated, the outcome is "negative side effects," and the cohort is individuals with "early stages of ovarian cancer." Additionally, in the illustrated embodiment, the RES 140B includes a weight. In embodiments, this weight is based on a variety of factors, including the confidence of the NLP, the publication characteristics of the document, and the like.

Figure 4:
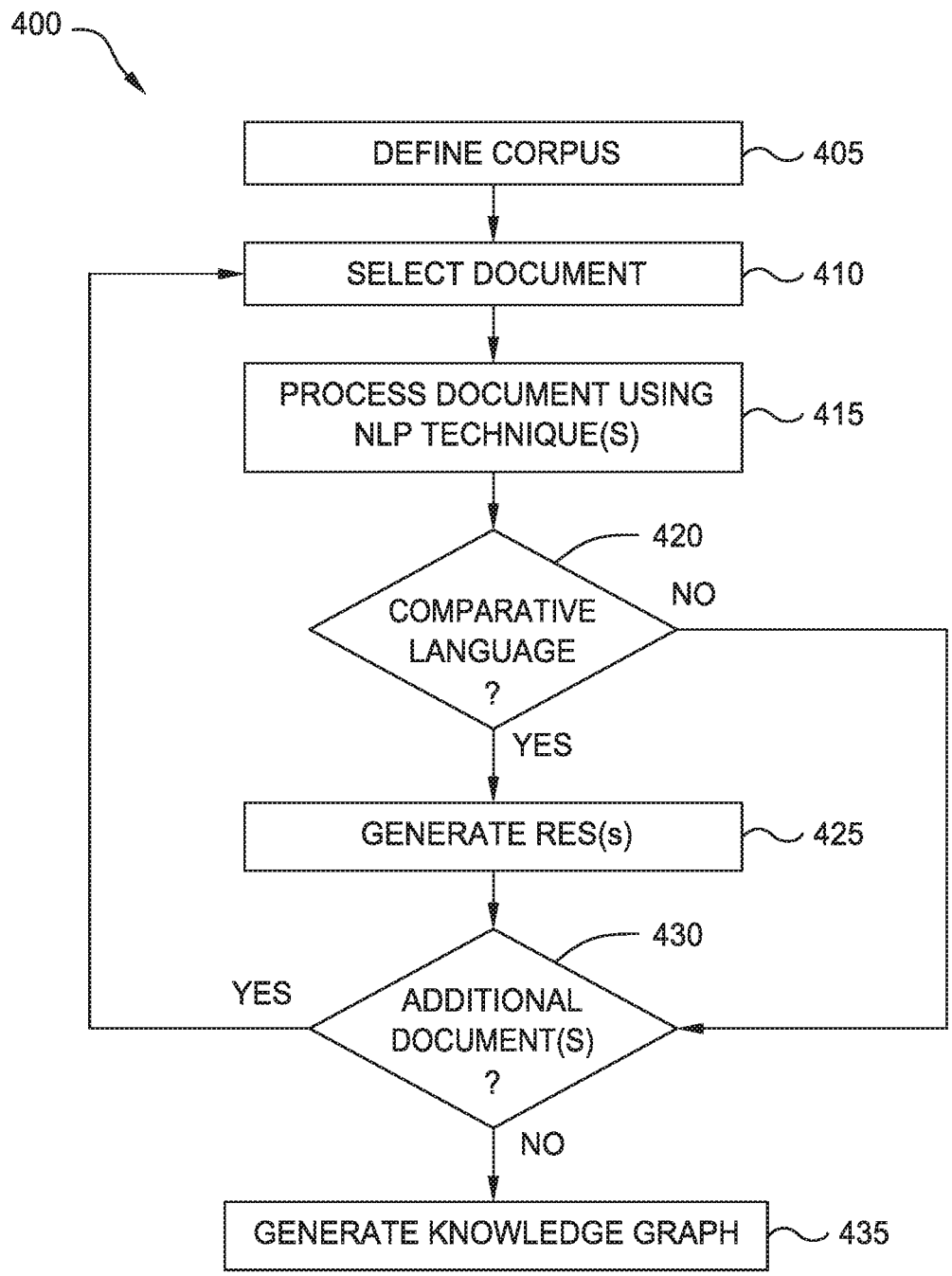
FIG. 4 illustrates a flow diagram illustrating a method for determining relative efficacies of various therapies, according to one embodiment disclosed herein.

FIG. 4 is a flow diagram illustrating a method 400 for determining relative efficacies of various therapies, according to one embodiment disclosed herein. The method 400 begins at block 405, where the Cognitive Interpretation Application 105 defines the relevant corpus. In one embodiment, this is based on a corpus indicated by the user or administrator. In some embodiments, the Cognitive Interpretation Application 105 receives one or more search terms, and builds the relevant corpus by searching or querying a larger corpus based on the search terms. In some embodiments, the Cognitive Interpretation Application 105 determines a set of documents in the identified corpus or sub-corpus that have not yet been processed or ingested. For example, in one embodiment, a user can indicate a disorder or search term, and the Cognitive Interpretation Application 105 can first identify documents relating to the indicated terms, and then identify documents in the corpus that have not already been processed and ingested. In this way, the Cognitive Interpretation Application 105 can selectively analyze new documents in order to update and refine the knowledge base. Once the relevant corpus has been defined, the method 400 proceeds to block 410.

At block 410, the Cognitive Interpretation Application 105 selects a document from the corpus. At block 415, the Cognitive Interpretation Application 105 processes the all or a portion of the selected document using one or more NLP techniques. As discussed above, in some embodiments, the Cognitive Interpretation Application 105 analyzes specified portions of each document. In some embodiments, if no comparisons are found (or if one or more identified comparative statements are missing information or detail), the Cognitive Interpretation Application 105 can process additional sections or text. In one embodiment, the Cognitive Interpretation Application 105 also annotates the extracted excerpts during block 415. The method 400 then proceeds to block 420.

At block 420, the Cognitive Interpretation Application 105 determines whether the selected document (or the portion that was analyzed) includes any comparative statements. If so, the method 400 continues to block 425. If not, the method 400 proceeds to block 430. At block 425, the Cognitive Interpretation Application 105 generates one or more RESs 140 for each of the identified comparative statements found. The method 400 then continues to block 430. At block 430, the Cognitive Interpretation Application 105 determines whether there is at least one additional document in the corpus that is yet to be processed. If so, the method 400 returns to block 410. Otherwise, the method 400 continues to block 435, where the Knowledge Graph Component 110 generates (or updates) a knowledge graph.

Figure 5:
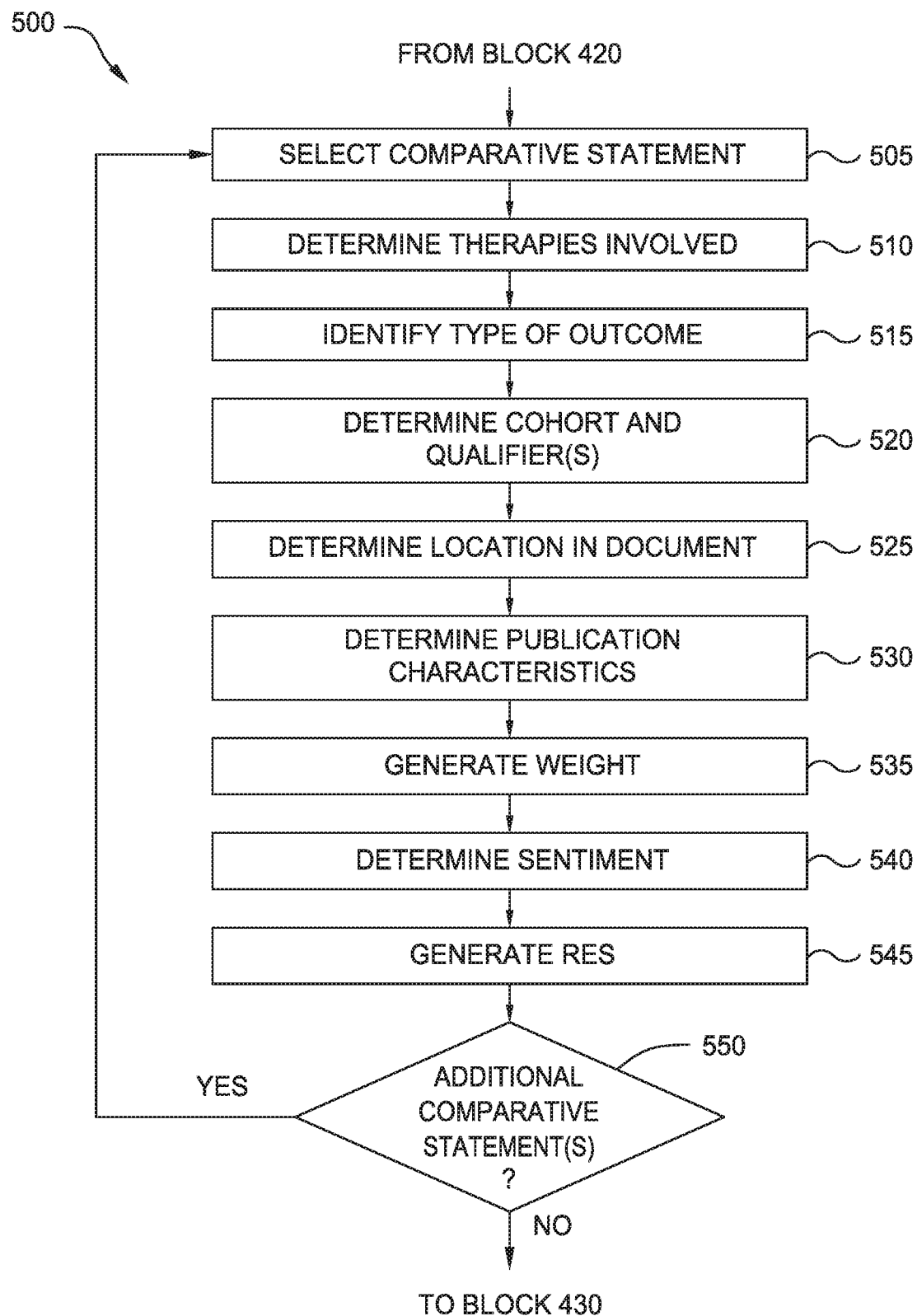
FIG. 5 is a flow diagram illustrating a method for generating relative efficacy structures summarizing comparisons between therapies, according to one embodiment disclosed herein.

FIG. 5 is a flow diagram illustrating a method 500 for generating RESs 140 summarizing comparisons between therapies, according to one embodiment disclosed herein. In one embodiment, the method 500 provides additional detail for block 425 in FIG. 4. The method 500 begins at block 505, where the Cognitive Interpretation Application 105 selects one of the comparative statements that were identified in the selected document. At block 510, the Cognitive Interpretation Application 105 identifies the therapies that are implicated by the selected statement. In one embodiment, the Cognitive Interpretation Application 105 utilizes NLP techniques to identify the relevant therapies. As discussed above, in some embodiments, the Cognitive Interpretation Application 105 parses other sections of the document, and/or other documents and data, in order to disambiguate any unknown or uncertain terms (e.g., ambiguous phrases or acronyms). The method 500 then continues to block 515.

At block 515, the Cognitive Interpretation Application 105 identifies the type of outcome the statement is addressing. That is, the Cognitive Interpretation Application 105 determines the particular outcome or effect that the selected statement is referring to. For example, in a medical embodiment, the outcomes can include overall survival, progression-free survival, remission, cure, death, complications, side effects, and the like. The method 500 then continues to block 520, where the Cognitive Interpretation Application 105 determines the cohort and/or cohort qualifiers that are relevant to the statement. For example, the cohort may be determined based on the patients being studied (e.g., as indicated by criteria used by the study authors when enrolling patients), and the cohort qualifiers can include any additional limitations included in the statement (e.g., "only patients above 65 saw a significant improvement.").

At block 525, the Cognitive Interpretation Application 105 determines the location in the selected document where the selected comparative statement was found. In one embodiment, block 525 comprises determining the section that the statement was in. In an embodiment, the sections are identified based on defined headings, metadata tags, and the like. In some embodiments, the weight of the generated RES 140 is adjusted based on the location. That is, in one embodiment, each section is associated with a respective weight or scale. For example, in one embodiment, the conclusion and abstract sections may be afforded higher weight than the general discussion section.

The method 500 then continues to block 530, where the Cognitive Interpretation Application 105 determines publication characteristics of the selected document that the statement was found in. For example, in one embodiment, the publication characteristics include a date when the document was published, the identity of the publisher, whether it has been peer-reviewed, and the like. In some embodiments, the publication characteristics also include the location in the document where the comparative statement was found. At block 535, the Cognitive Interpretation Application 105 generates a weight for the RES 140 based on the publication characteristics, and/or the determined location. In some embodiments, the Cognitive Interpretation Application 105 also considers any confidence values generated by the NLP models when parsing the text. Further, in one embodiment, the weight is based in part on the strength of the comparator used (e.g., whether the treatment is "slightly better" or "far superior").

The method 500 then continues to block 540, where the Cognitive Interpretation Application 105 determines the sentiment of the statement. In an embodiment, as discussed above, the Cognitive Interpretation Application 105 utilizes NLP to classify the statement as positive, negative, or neutral. Finally, at block 545, the Cognitive Interpretation Application 105 generates a RES 140 for the selected comparative statement based on the determined attributes, sentiment, and weight. At block 550, the Cognitive Interpretation Application 105 determines whether there is at least one additional comparative statement found in the document. If so, the method 500 returns to block 505. Otherwise, the method 500 terminates.

Figure 6:
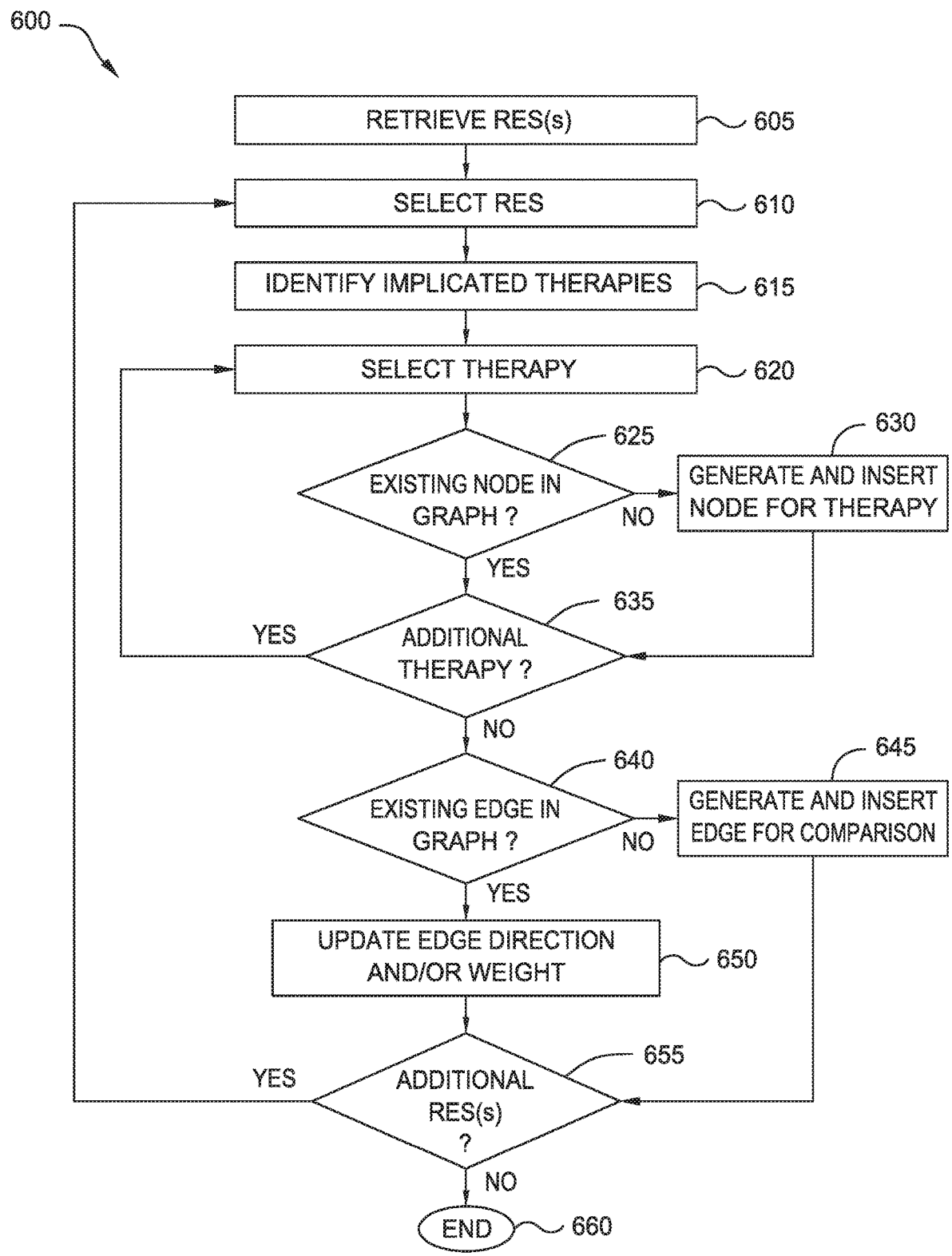
FIG. 6 is a flow diagram illustrating a method for generating a knowledge graph based on generated relative efficacy structures, according to one embodiment disclosed herein.

FIG. 6 is a flow diagram illustrating a method 600 for generating a knowledge graph based on generated relative efficacy structures, according to one embodiment disclosed herein. The method 600 begins at block 605, where the Knowledge Graph Component 110 retrieves one or more RES(s) 140 that were generated by the Cognitive Interpretation Application 105. At block 610, the Knowledge Graph Component 110 selects one of the RESs 140. The method 600 then proceeds to block 615, where the Knowledge Graph Component 110 identifies the therapies that are indicated by the selected RES 140. That is, the Knowledge Graph Component 110 determines which therapies are compared in the RES 140. At block 620, the Knowledge Graph Component 110 selects one of these identified therapies.

The method 600 continues to block 625, where the Knowledge Graph Component 110 determines whether there is an existing node in the knowledge graph for the selected therapy. As discussed above, in an embodiment, each node in the knowledge graph corresponds to a therapy. In some embodiments, a therapy can include a combination of treatments or mediations (e.g., a drug as well as physical therapy). If the selected therapy is already represented in the knowledge graph, the method 600 continues to block 635. If the selected therapy is not yet in the knowledge graph, the method 600 proceeds to block 630, where the Knowledge Graph Component 110 generates and inserts a new node into the graph to represent the selected therapy. The method 600 then continues to block 635.

At block 635, the Knowledge Graph Component 110 determines whether there are additional therapies in the selected RES 140. If so, the method 600 returns to block 620. Otherwise, the method 600 continues to block 640. In the illustrated embodiment, the Knowledge Graph Component 110 analyzes each therapy, and generates new nodes for each. In some embodiments, the knowledge graph is already constructed using a known or defined set of therapies. In such an embodiment, the Knowledge Graph Component 110 does not generate and insert new nodes. In some embodiments, in addition to an existing set of therapies, the Knowledge Graph Component 110 can further generate and insert nodes representing new therapies or new combinations of treatments that are identified in the RES 140.

In one embodiment, each node in the knowledge graph can be connected to zero or more other nodes, based on whether a comparison has been identified between the corresponding therapies. For example, in one embodiment, if two therapies have not been directly compared in the published literature, there will be no link or connection between the corresponding nodes. If, however, the therapies have been compared at least once, there will be an edge or connection between them. In some embodiments, each edge includes a number of dimensions indicating the directionality, the cohort(s) the edge applies to, the outcome(s) the edge applies to, and the like. For example, in such an embodiment, an edge may indicate that treatment A is better than treatment B, with respect to overall survival, in patients over 65. For patients under 65, however, there may be no edge or connection (if the therapies have not been compared for patients under 65), or there may be a link indicating that treatment B is better than treatment A. Similarly, with respect to a different outcome (such as progression-free survival or side effects), there may be no link, or a different link or connection may indicate that treatment B is better than treatment A. In some embodiments, the knowledge graph is constructed with a single edge connecting each pair of therapies, where that edge identifies all documents and/or RESs 140 that included a statement comparing the respective therapies. In another embodiment, the graph can include a respective edge to represent each respective RES 140 that is relevant to the respective pair of therapies.

In some embodiments, each edge in the graph is associated with a respective weight. This weight can be based on a variety of factors, including the number of times the relationship has been identified (e.g., the number of RESs 140 associated with the particular edge), the confidence or weight of each of those RESs 140, and the like. In some embodiments, as additional RESs 140 indicate the same relative efficacy (e.g., that one therapy is better than the other), the weight or strength of the edge is progressively strengthened. If, however, a RES 140 indicates the opposite comparison (e.g., that the first therapy is worse than the other), the weight or strength of the edge is reduced. In this way, each connection in the graph indicates an overall relative efficacy of the therapies, along with an associated strength or confidence in the accuracy of the comparison.

At block 640, the Knowledge Graph Component 110 determines whether there is an existing edge in the knowledge graph representing the relationship indicated by the selected RES 140. That is, in an embodiment, the Knowledge Graph Component 110 determines whether there is any link or connection between the identified therapies, with respect to the indicated cohort and outcome, regardless of the directionality of the relationship (e.g., regardless of whether the existing link matches the determined relative efficacy in the RES 140). In an embodiment, there may be any number of connections between the identified therapies with respect to other cohorts or other outcomes. The determination at block 640, however, is specific to the particular cohort and outcome specified in the RES 140.

In some embodiments, a particular RES 140 can include multiple comparisons. For example, if a statement included that treatment A was superior than all known treatments, the Cognitive Interpretation Application 105 can parse or analyze existing literature (or one or more knowledge graphs) to identify known treatments with respect to the disorder, cohort, and outcome. In such an embodiment, the RES 140 can include an indication of each of these known treatments. In other embodiments, a separate RES 140 is created for each of the comparisons (e.g., for each of the known treatments). In an embodiment, if the RES 140 includes comparisons to multiple therapies, the process discussed below (and reflected by blocks 640, 645, and 650) is repeated for each.

If the Knowledge Graph Component 110 determines, at block 640, that there is no edge in the graph representing the comparison, with respect to the identified cohort and outcome, the method 600 continues to block 645, where the Knowledge Graph Component 110 generates and inserts one. In one embodiment, the directionality of the new edge is based on the sentiment reflected in the selected RES 140 (e.g., positive, negative, or neutral). Further, in an embodiment, the initial weight or strength of the new edge is based on the weight or confidence of the RES 140. In this way, the knowledge graph is updated to reflect that the published literature includes a direct comparison between the therapies, and indicates the relative efficacy of the therapies (e.g., based on the directionality of the edge).

If the Knowledge Graph Component 110 determines, at block 640, that an edge already exists for the indicated comparison, with respect to the specified cohort and outcome, the method 600 continues to block 650, where the Knowledge Graph Component 110 updates the weight and/or direction of the identified edge. In some embodiments, the Knowledge Graph Component 110 instead inserts a new edge, depending on the particular design that will be used to represent multiple comparisons between two treatments in the knowledge graph. As discussed above, in one embodiment, this updating includes adjusting the weight of the edge based on the weight and directionality of the selected RES 140. In an embodiment, if the sentiment reflected by the RES 140 is in the same direction as the existing edge (e.g., the RES 140 and the edge agree that one treatment is superior), the weight or strength is increased. If the directions are opposite, the weight is decreased. Similarly, in one embodiment, if the selected RES 140 has a neutral sentiment (indicating that the therapies are equally effective), the weight of the edge is reduced, regardless of which direction it currently points. If the edge is already neutral, a neutral weight or strength can be increased, indicating that there is additional evidence that the therapies are equally effective.

In one embodiment, the amount that the edge strength is changed is dependent on the magnitude of the confidence or weight associated with the RES 140. If the RES 140 is associated with a high weight, the strength of the edge will be adjusted a greater amount than if the weight of the RES 140 was low. In one embodiment, if the weight falls below a predefined threshold (e.g., within a defined distance from zero), the edge is removed from the graph, indicating that there is no medical consensus regarding the relationship or relative efficacy. In other embodiments, the edge is updated to have no direction, reflecting that there is no solid consensus, and results are mixed (e.g., indicating that the comparison has been studied, but that there is no strong evidence supporting either therapy as more effective than the other). In some embodiments, this edge is retained with a low weight or strength, and is assigned a neutral sentiment to indicate that neither therapy is clearly superior to the other.

Similarly, in some embodiments, if an edge is neutral (or close to neutral) and the weight adjustment would cause the weight to be negative, the direction of the edge is switched, indicating a (potentially weak) new consensus that the relative efficacy of the treatments is reversed from the previously-understood comparison. In some embodiments, each edge in the graph is associated with a directionality as well as a weight or strength of the edge (representing the strength of the evidence). The method 600 then proceeds to block 655, where the Knowledge Graph Component 110 determines whether there is at least one additional RES 140 that has not been analyzed and ingested into the knowledge graph. If so, the method 600 returns to block 610 to select a next RES 140. Otherwise, the method 600 terminates at block 660. In this way, the Knowledge Graph Component 110 can update and refine the knowledge graph based on new therapies and studies. In embodiments, the knowledge graph is a multi-dimensional representation of the medical consensus as to relative efficacies of any number of therapies, with respect to any combination of particular cohorts and outcomes. Advantageously, embodiments of the present disclosure enable the graph to be continuously and rapidly updated when new published literature becomes available, such that the knowledge graph represents the most up-to-date and accurate representation possible. Further, because of the high-dimensionality of the graph (e.g., because the relative efficacies differ based on the individual cohort and outcome), the knowledge graph provides additional data that is far more granular, and is not otherwise available to healthcare providers.

In some embodiments, the knowledge graph can be accessed and searched by healthcare providers in order to determine optimal treatments for a particular patient. For example, in an embodiment, the provider can search the knowledge graph (e.g., using the User Interface 280 of the Client Device 255) to identify therapies and/or relative efficacies that are relevant to the cohort to which the patient belongs. That is, in an embodiment, the knowledge graph can be parsed to identify comparisons that are relevant to a patient in a particular cohort (e.g., having a particular set of attributes). In some embodiments, the provider can also filter, sort, or search the knowledge graph based on the desired outcome. In one embodiment, based on these relative efficacies, the therapies can be scored and ranked, in order to identify the most optimal therapy. This allows the provider to make improved decisions with respect to treating the patient.

In some embodiments, the outcomes types are associated with a predefined hierarchy. That is, some outcomes (e.g., progression-free survival) may be considered more important than other outcomes (e.g., side effects), and therefore be weighted more heavily when aggregating the relative efficacies with respect to each outcome in order to determine an overall relative efficacy (e.g., an overall optimal or best therapy, with respect to all outcomes). In such an embodiment, the ranking or scoring of the therapies may take into account the relative efficacies, as well as the importance or weight of the particular outcome. That is, although a first therapy may be the best with respect to side effects, it may be given a lower score than a second therapy that is better with respect to survival.

Figure 7:
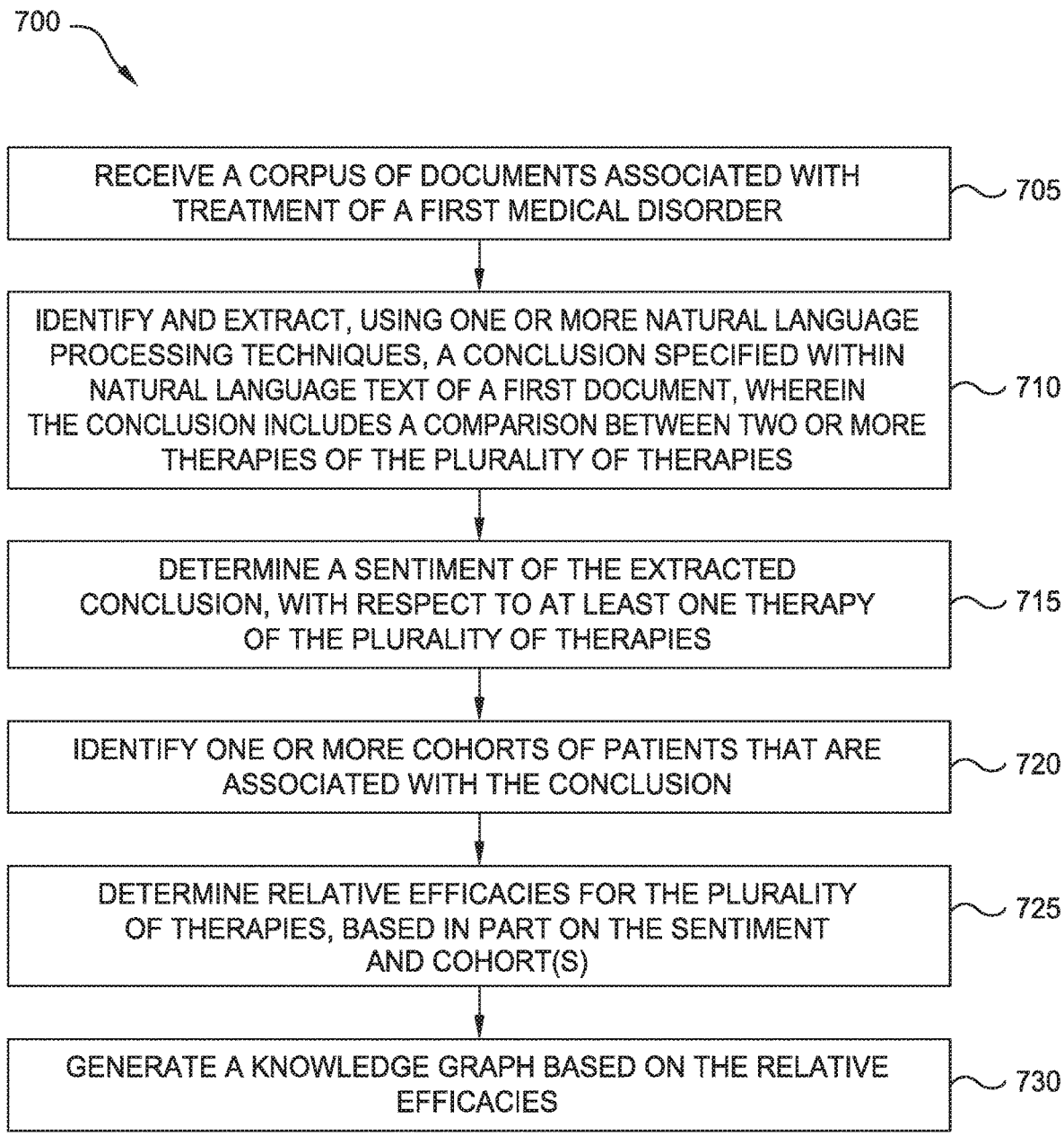
FIG. 7 is a flow diagram illustrating a method for cognitively determining relative efficacies of therapies, according to one embodiment disclosed herein.

FIG. 7 is a flow diagram illustrating a method 700 for cognitively determining relative efficacies of therapies, according to one embodiment disclosed herein. The method 700 begins at block 705, where the Cognitive Interpretation Application 105 receives a corpus of documents associated with treatment of a first medical disorder. At block 710, the Cognitive Interpretation Application 105 identifies and extracts, using one or more natural language processing techniques, a conclusion specified within natural language text of a first document, wherein the conclusion includes a comparison between two or more therapies of the plurality of therapies. The method 700 then continues to block 715, where the Cognitive Interpretation Application 105 determines a sentiment of the extracted conclusion, with respect to at least one therapy of the plurality of therapies. Further, at block 720, the Cognitive Interpretation Application 105 identifies one or more cohorts of patients that are associated with the conclusion. The method 700 proceeds to block 725, where the Cognitive Interpretation Application 105 determines relative efficacies for the plurality of therapies, based in part on the sentiment and cohort(s). Finally, at block 730, the Knowledge Graph Component generates a knowledge graph based on the relative efficacies.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the preceding features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the Cognitive Interpretation Application 105) or related data available in the cloud. For example, the Cognitive Interpretation Application 105 could execute on a computing system in the cloud and analyze literature to generate RESs. In such a case, the Cognitive Interpretation Application 105 could determine the relative efficacies of therapies, and store the efficacies at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method comprising:
   receiving a corpus of documents associated with treatment of a first medical disorder;
   generating, by operation of one or more processors, a plurality of relative efficacy structures for a plurality of therapies by, for at least a first respective document in the corpus of documents:
   identifying and extracting, using one or more natural language processing techniques, a conclusion specified within natural language text of the respective document, wherein the conclusion includes a comparison between two or more therapies of the plurality of therapies;
   determining, for each respective therapy of the plurality of therapies, a respective sentiment of the extracted conclusion by using one or more natural language processing techniques, wherein at least one determined sentiment is classified as neutral; and
   identifying one or more cohorts of patients that are associated with the conclusion; and
   generating a knowledge graph based on the plurality of relative efficacy structures, comprising:
   identifying a first, second, and third therapy, of the plurality of therapies, specified by a first relative efficacy structure of the plurality of relative efficacy structures;
   upon determining that the first therapy is not represented in the knowledge graph, generating and inserting a node for the first therapy;
   upon determining that an edge does not exist between the first therapy and the second therapy in the knowledge graph, generating and inserting an edge connecting nodes corresponding to the first and second therapies, based on the first relative efficacy structure; and
   upon determining that an edge exists between the second therapy and the third therapy in the knowledge graph, updating a weight of the edge based on a weight and directionality specified by the first relative efficacy structure, wherein updating the weight causes the edge between the second and third therapies to change directions.

2. The method of claim 1, wherein receiving the corpus of documents comprises querying a larger corpus based on the first medical disorder, such that the generated corpus of documents includes documents that are clinically relevant to the first medical disorder.

3. The method of claim 1, wherein identifying the conclusion of the respective document comprises:
  identifying comparative language in the respective document; and
  determining a section in the respective document where the comparative language is located, wherein generating the knowledge graph is based further on the section in the respective document where the comparative language is located.

4. The method of claim 1, wherein extracting the conclusion of the respective document comprises:
  identifying an unknown term, wherein the unknown term is either (i) an ambiguous term, or (ii) an acronym; and
  analyzing the respective document to determine a meaning for the unknown term.

5. The method of claim 1, wherein determining the sentiment of the extracted conclusion with respect to the at least one therapy comprises classifying the extracted conclusion as positive, negative, or neutral.

6. The method of claim 1, the method further comprising determining one or more publication characteristics of the respective document.

7. The method of claim 6, wherein generating the knowledge graph comprises:
  aggregating the plurality of relative efficacy structures, wherein each of the plurality of relative efficacy structures is weighted based on the publication characteristics of the respective document from which the relative efficacy structure was generated.

8. The method of claim 1, wherein the comparison between two or more therapies is with respect to one or more outcome types, of a plurality of outcome types, wherein the plurality of outcome types is associated with a predefined hierarchy.

9. The method of claim 8, the method further comprising:
  receiving a set of patient attributes for a first patient;
  determining a cohort of the first patient;
  identifying a plurality of potential therapies for the first patient by parsing the knowledge graph based on the cohort of the first patient;
  ranking the plurality of potential therapies, based on a set of relative efficacy structures associated with each of the plurality of potential therapies and based further on the predefined hierarchy; and
  providing the ranked plurality of potential therapies to a user.

10. A computer program product comprising a computer-readable storage medium having computer-readable program code embodied therewith, the computer-readable program code executable by one or more computer processors to perform an operation comprising:
  receiving a corpus of documents associated with treatment of a first medical disorder;
  generating a plurality of relative efficacy structures for a plurality of therapies by, for at least a first respective document in the corpus of documents:
    identifying and extracting, using one or more natural language processing techniques, a conclusion specified within natural language text of the respective document, wherein the conclusion includes a comparison between two or more therapies of the plurality of therapies;
    determining, for each respective therapy of the plurality of therapies, a respective sentiment of the extracted conclusion by using one or more natural language processing techniques, wherein at least one determined sentiment is classified as neutral; and
    identifying one or more cohorts of patients that are associated with the conclusion; and
  generating a knowledge graph based on the plurality of relative efficacy structures, comprising:
    identifying a first, second, and third therapy, of the plurality of therapies, specified by a first relative efficacy structure of the plurality of relative efficacy structures;
    upon determining that the first therapy is not represented in the knowledge graph, generating and inserting a node for the first therapy;
    upon determining that an edge does not exist between the first therapy and the second therapy in the knowledge graph, generating and inserting an edge connecting nodes corresponding to the first and second therapies, based on the first relative efficacy structure; and
    upon determining that an edge exists between the second therapy and the third therapy in the knowledge graph, updating a weight of the edge based on a weight and directionality specified by the first relative efficacy structure, wherein updating the weight causes the edge between the second and third therapies to change directions.

11. The computer program product of claim 10, wherein identifying the conclusion of the respective document comprises:
  identifying comparative language in the respective document; and
  determining a section in the respective document where the comparative language is located, wherein generating the knowledge graph is based further on the section in the respective document where the comparative language is located.

12. The computer program product of claim 10, wherein extracting the conclusion of the respective document comprises:
  identifying an unknown term, wherein the unknown term is either (i) an ambiguous term, or (ii) an acronym; and
  analyzing the respective document to determine a meaning for the unknown term.

13. The computer program product of claim 10, wherein determining the sentiment of the extracted conclusion with respect to the at least one therapy comprises classifying the extracted conclusion as positive, negative, or neutral.

14. The computer program product of claim 10, wherein the comparison between two or more therapies is with respect to one or more outcome types, of a plurality of outcome types, wherein the plurality of outcome types is associated with a predefined hierarchy.

15. The computer program product of claim 14, the operation further comprising:
  receiving a set of patient attributes for a first patient;
  determining a cohort of the first patient;
  identifying a plurality of potential therapies for the first patient by parsing the knowledge graph based on the cohort of the first patient;
  ranking the plurality of potential therapies, based on a set of relative efficacy structures associated with each of the plurality of potential therapies and based further on the predefined hierarchy; and
  providing the ranked plurality of potential therapies to a user.

16. A system comprising:
  one or more computer processors; and a memory containing a program which when executed by the one or more computer processors performs an operation, the operation comprising:

receiving a corpus of documents associated with treatment of a first medical disorder;

generating a plurality of relative efficacy structures for a plurality of therapies by, for at least a first respective document in the corpus of documents:

identifying and extracting, using one or more natural language processing techniques, a conclusion specified within natural language text of the respective document, wherein the conclusion includes a comparison between two or more therapies of the plurality of therapies;

determining, for each respective therapy of the plurality of therapies, a respective sentiment of the extracted conclusion by using one or more natural language processing techniques, wherein at least one determined sentiment is classified as neutral; and identifying one or more cohorts of patients that are associated with the conclusion; and generating a knowledge graph based on the plurality of relative efficacy structures, comprising:

identifying a first, second, and third therapy, of the plurality of therapies, specified by a first relative efficacy structure of the plurality of relative efficacy structures;

upon determining that the first therapy is not represented in the knowledge graph, generating and inserting a node for the first therapy;

upon determining that an edge does not exist between the first therapy and the second therapy in the knowledge graph, generating and inserting an edge connecting nodes corresponding to the first and second therapies, based on the first relative efficacy structure; and upon determining that an edge exists between the second therapy and the third therapy in the knowledge graph, updating a weight of the edge based on a weight and directionality specified by the first relative efficacy structure, wherein updating the weight causes the edge between the second and third therapies to change directions.

17. The system of claim 16, wherein identifying the conclusion of the respective document comprises:

identifying comparative language in the respective document; and determining a section in the respective document where the comparative language is located, wherein generating the knowledge graph is based further on the section in the respective document where the comparative language is located.

18. The system of claim 16, wherein extracting the conclusion of the respective document comprises:

identifying an unknown term, wherein the unknown term is either (i) an ambiguous term, or (ii) an acronym; and analyzing the respective document to determine a meaning for the unknown term.

19. The system of claim 16, wherein determining the sentiment of the extracted conclusion with respect to the at least one therapy comprises classifying the extracted conclusion as positive, negative, or neutral.

20. The system of claim 16, wherein the comparison between two or more therapies is with respect to one or more outcome types, of a plurality of outcome types, wherein the plurality of outcome types is associated with a predefined hierarchy, and wherein the operation further comprises:

receiving a set of patient attributes for a first patient;

determining a cohort of the first patient;

identifying a plurality of potential therapies for the first patient by parsing the knowledge graph based on the cohort of the first patient;

ranking the plurality of potential therapies, based on a set of relative efficacy structures associated with each of the plurality of potential therapies and based further on the predefined hierarchy; and providing the ranked plurality of potential therapies to a user.

* * * * *